United States Patent
Venkataramanan et al.

(10) Patent No.: US 8,587,302 B2
(45) Date of Patent: Nov. 19, 2013

(54) MODIFIED PULSE SEQUENCE TO ESTIMATE PROPERTIES

(75) Inventors: Lalitha Venkataramanan, Lexington, MA (US); Tarek M. Habashy, Burlington, MA (US); Denise Freed, Newton Highlands, MA (US); Ashok Belani, Paris (FR)

(73) Assignee: Schlumberger Technology Corporation, Sugar Land, TX (US)

(*) Notice: Subject to any disclaimer, the term of this patent is extended or adjusted under 35 U.S.C. 154(b) by 597 days.

(21) Appl. No.: 12/717,512

(22) Filed: Mar. 4, 2010

(65) Prior Publication Data

US 2011/0215802 A1   Sep. 8, 2011

(51) Int. Cl.
*G01V 3/00* (2006.01)
*G01V 1/48* (2006.01)

(52) U.S. Cl.
USPC ....... 324/303; 702/8; 702/9; 702/12; 324/300

(58) Field of Classification Search
USPC ................................. 324/300–322; 702/6–31
See application file for complete search history.

(56) References Cited

U.S. PATENT DOCUMENTS

| | | | |
|---|---|---|---|
| 6,005,389 A * | 12/1999 | Prammer | 324/303 |
| 6,600,316 B2 * | 7/2003 | Chen et al. | 324/303 |
| 6,891,369 B2 * | 5/2005 | Hurlimann et al. | 324/303 |
| 7,049,815 B2 | 5/2006 | Itskovich et al. | |
| 7,305,306 B2 | 12/2007 | Venkataramanan et al. | |
| 7,804,296 B2 * | 9/2010 | Flaum et al. | 324/303 |
| 2002/0105326 A1 | 8/2002 | Hurlimann et al. | |
| 2005/0270023 A1 * | 12/2005 | Freedman | 324/303 |
| 2006/0155472 A1 | 7/2006 | Venkataramanan et al. | |
| 2008/0314582 A1 | 12/2008 | Belani et al. | |
| 2010/0043538 A1 * | 2/2010 | Cheng et al. | 73/54.42 |
| 2010/0259258 A1 * | 10/2010 | Fransson et al. | 324/303 |

OTHER PUBLICATIONS

International Search Report and Written Opinion of PCT Application Serial No. PCT/US2011/026008 dated Nov. 24, 2011: pp. 1-8.
Freed, "Dependence on chain length of NMR relaxations times in mixtures of alkanes," J. Chem. Phys., 2007, vol. 126: pp. 174502-1-174502-10.
Song et al, "Determining the resolution of Laplace inversion spectrum," J. Chem. Phys., 2005, vol. 122: pp. 104104-1-104104-8.
Allen et al., "How to Use Borehole Nuclear Magnetic Resonance," Oilfield Review, Summer 1997: pp. 34-57.
Fordham et al., "Imaging Multiexponential Relaxation in the (y1 loge T1) Plane, with Application to Clay Filtration in Rock Cores," Journal of Magnetic Resonance, 1995, Series A vol. 113: pp. 139-150.

(Continued)

*Primary Examiner* — Jermele M Hollington
*Assistant Examiner* — Emily Chan
(74) *Attorney, Agent, or Firm* — Rachel E. Greene; Jakub Michna; Bridget Laffey

(57) ABSTRACT

Methods and related systems are described for estimating fluid or rock properties from NMR measurements. A modified pulse sequence is provided that can directly provide moments of relaxation-time or diffusion distributions. This pulse sequence can be adapted to the desired moment of relaxation-time or diffusion coefficient. The data from this pulse sequence provides direct estimates of fluid properties such as average chain length and viscosity of a hydrocarbon. In comparison to the uniformly-spaced pulse sequence, these pulse sequences are faster and have a lower error bar in computing the fluid properties.

40 Claims, 7 Drawing Sheets

(56) References Cited

OTHER PUBLICATIONS

Press et al., "18.5: Linear Regularization Methods," Numerical Recipes in C: The Art of Scientific Computing Second Edition, New York: Cambridge University Press, 1992: pp. 808-815.

Hürlimann et al., "Quantitative Measurement of Two-Dimensional Distribution Functions of Diffusion and Relaxation n Grossly Inhomogeneous Fields," Journal of Magnetic Resonance, 2002, vol. 157: pp. 31-42.

Freed et al., "Scaling Laws for Diffusion Coefficients in Mixtures of Alkanes," Physical Review Letters, Feb. 2005, PRL 94: pp. 067602-1-067602-4.

Venkataramanan et al., "Solving Fredholm Integrals of the First Kind With Tensor Product Structure in 2 and 2.5 Dimensions," IEEE Transactions on Signal Processing, May 2002, vol. 50(5): pp. 1017-1026.

Venkataramanan et al., "Method to Estimate a Sample Properties from Exponentially Decaying Data," U.S. Appl. No. 61/242,218, filed Sep. 14, 2009: pp. 1-30.

* cited by examiner

MODIFIED PULSE SEQUENCE TO ESTIMATE PROPERTIES

BACKGROUND

1. Field

This patent specification relates to estimating properties from exponentially decaying data. More particularly, this patent specification relates to methods and systems for estimating material properties from a non-uniform sequence of excitations, such as with NMR measurements.

2. Background

Traditionally, fluid properties using Nuclear Magnetic Resonance (NMR) are obtained by study of longitudinal or transverse relaxation or diffusion measurements. Longitudinal ($T_1$) relaxation data are acquired using an inversion-recovery pulse sequence where the recovery times are often chosen arbitrarily. Transverse ($T_2$) relaxation data are acquired using the CPMG pulse sequence with pulses that are typically uniformly spaced in the time-domain. There is no clear mathematical methodology for choosing the acquisition times at which the diffusion measurements are obtained. The relaxation or diffusion data thus obtained from these pulse sequences are used to infer the relaxation time or diffusion distributions. In turn, these distributions are used to infer petrophysical or hydrocarbon properties.

Traditional well-logging using NMR is employed to infer petro-physical and fluid properties of the formation or in-situ hydrocarbon. The multi-exponential time-decay of NMR magnetization is characterized by relaxation time constants $T_1$, $T_2$ or diffusion D and corresponding amplitudes $f_{T_1}(T_1)$, $f_{T_2}(T_2)$ or $f_D(D)$. Since the relaxation times and/or diffusion constants are expected to be continuous and typically span several decades, these amplitudes are often referred to as relaxation-time or diffusion distributions. These distributions provide a wealth of information about both the rock as well as fluid properties. See e.g. D. Allen, S. Crary, and R. Freedman, *How to use borehole Nuclear Magnetic Resonance*, Oilfield Review, pages 34-57, 1997.

An NMR measurement consists of a sequence of transverse magnetic pulses transmitted by an antenna. Typically, the CPMG pulse sequence is used to measure $T_2$ relaxation. It consists of a pulse that tips hydrogen protons 90° and is followed by several thousand pulses that refocus the protons by tipping them 180°. The data are acquired by an antenna between the evenly spaced 180° pulses and are thus uniformly spaced in time. On the other hand, the $T_1$ relaxation is studied using the inversion-recovery pulse sequence. There is no specific rule for choosing the recovery times. See, Y. Q. Song, L. Venkataramanan, and L. Burcaw, *Determining the resolution of Laplace inversion spectrum*, Journal of Chemical Physics, page 104104, 2005. Similarly, there is no clear mathematical framework to optimally choose the acquisition times for diffusion measurements.

The data acquired from all of the above pulse sequences can be represented by a Fredholm integral (see, M. D. Hurlimann and L. Venkataramanan, *Quantitative measurement of two dimensional distribution functions of diffusion and relaxation in grossly homogeneous fields*, Journal Magnetic Resonance, 157:31-42, July 2002 and L. Venkataramanan, Y. Q. Song, and M. D. Hurlimann, *Solving Fredholm integrals of the first kind with tensor product structure in 2 and 2.5 dimensions*, IEEE Transactions on Signal Processing, 50:1017-1026, 2002, hereinafter "Venkataramanan et al. 2002"), $$M(t) = \int_0^\infty e^{-t/x} f_x(x) dx \qquad (1)$$

where the variable x typically refers to $T_1$, $T_2$, or 1/D. See, Venkataramanan et al. 2002. Thus the measured data in eqn. (1) is related to a Laplace transform of the unknown underlying function $f_x(x)$.

Scaling laws established on mixtures of alkanes provide a relation between fluid composition and relaxation time and/or diffusion coefficients of the components of the mixture (see D. E. Freed, *Scaling laws for diffusion coefficients in mixtures of alkanes*, Physical Review Letters, 94:067602, 2005, and D. E. Freed, *Dependence on chain length of NMR relaxation times in mixtures of alkanes*, Journal of Chemical Physics, 126:174502, 2007). A typical crude oil has a number of components, such as methane, ethane etc. Let $N_i$ refer to the number of carbon atoms or chain length of the i-th component. Let $\overline{N}$ denote the molar average chain length of the crude oil, also defined as the harmonic mean of the chain lengths, $$\frac{1}{\overline{N}} \equiv \sum_{i=1}^\infty \frac{f_N(N_i)}{N_i} = \langle N^{-1} \rangle \qquad (2)$$

where $f_N(N_i)$ denotes the mass fraction of component i in the hydrocarbon. According to the scaling law, the bulk relaxation time $T_{2,i}$ of component i in a crude oil follows a power law and depends inversely on its chain length or number of carbon atoms, $N_i$. Thus, the larger the molecule, the smaller the relaxation time $T_{2,i}$. The relaxation time also depends inversely on the average chain length $\overline{N}$ of the hydrocarbon, according to $$T_{2,i} = BN_i^{-\kappa}\overline{N}^{-\gamma} \qquad (3)$$

In eqn. (3), parameters B, $\gamma$ and $\kappa$ are constants at a given pressure and temperature. Similarly, if $D_i$ refers to the diffusion coefficient of component i, $$D_i = AN_i^{-\nu}\overline{N}^{-\beta} \qquad (4)$$

where A, $\nu$ and $\beta$ and are constants at a given pressure and temperature. The scaling theory can also be used to derive an expression for fluid viscosity, $$\eta \propto \langle D^{-1}\rangle \Rightarrow \eta \propto \overline{N}^\beta \langle N^\nu \rangle. \qquad (5)$$

Traditional analysis of the measured NMR data to obtain fluid properties goes as follows. The inverse Laplace transform of eqn. (1) is performed to estimate the probability density function $f_x(x)$ from the measured data. Next, using eqns. (3)-(5), the average chain length $\overline{N}$ and the chain length distribution $f_N(N)$ are computed. Viscosity $\eta$ of the hydrocarbon is then estimated using eqn. (5). This traditional analysis has some disadvantages. First, the inverse Laplace transform of the measured NMR data in eqn. (1) is non-linear due to the non-negativity constraint on $f_x(x)$. See, Venkataramanan et al. 2002, and E. J. Fordham, A. Sezginer, and L. D. Hall, *Imaging multiexponential relaxation in the (y, $log_e T_1$) plane, with application to clay filtration in rock cores*, J. Mag. Resonance A, 113:139-150, 1995. Next, it is also mathematically ill-conditioned. Often, regularization or prior information about the expected solution is incorporated into the problem formulation to make it better conditioned. However, the choice of the regularization functional as well as the weight given to the prior information is a well-known drawback of this transform due to its non-uniqueness. See, W. H. Press, S. A. Teukolsky, and W. T. Vetterling, *Numerical Recipes in C*, Cambridge University Press, 1992. Thus errors in the estimation of $T_1$, $T_2$, or D distributions are propagated into errors in the estimation of fluid properties.

SUMMARY

According to some embodiments, a method for estimating a property of a material is provided. A measurable change in the material is induced and measurements are made of an aspect of the material that tends to exponentially decay following the induction. The induction is repeated at predetermined intervals, and the material property is estimated based on measurements of the aspect. The intervals are designed so as to improve the estimation of the property.

The induction can be a transmitted transverse magnetic pulse as with NMR measurements, according to some embodiments. According to some embodiments the induction is the induction of a pressure or temperature change in the material. According to some embodiments, the interval spacing (e.g. in time, in frequency, etc.) is designed according to a formula determined by the property being estimated, and the spacing is non-uniform in both linear and logarithmic scales. According to some embodiments the interval spacing in time follows a power law and allows for the material property to be directly computed from the measurements.

The method can be carried out as part of an oilfield service, and the measurements can be made downhole. The material can be a fluid, a solid or a mixture. According to some embodiments, the material is one or more rock solids and the material properties being estimated are petrophysical properties of the rock solids.

According to some embodiments, a system for estimating a property of a material is provided that includes an inducer that is adapted to induce a measurable change in the material, and one or more sensors adapted to measure an aspect of the material that tends to exponentially decay following an induction. A controller is coupled to the inducer, and adapted and programmed to repeat the induction at predetermined intervals. A processing system is adapted to estimate the material property based on measurements. The induction intervals are designed so as to improve the estimation of the property.

Further features and advantages will become more readily apparent from the following detailed description when taken in conjunction with the accompanying drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION OF THE PREFERRED EMBODIMENTS

Figure 1:
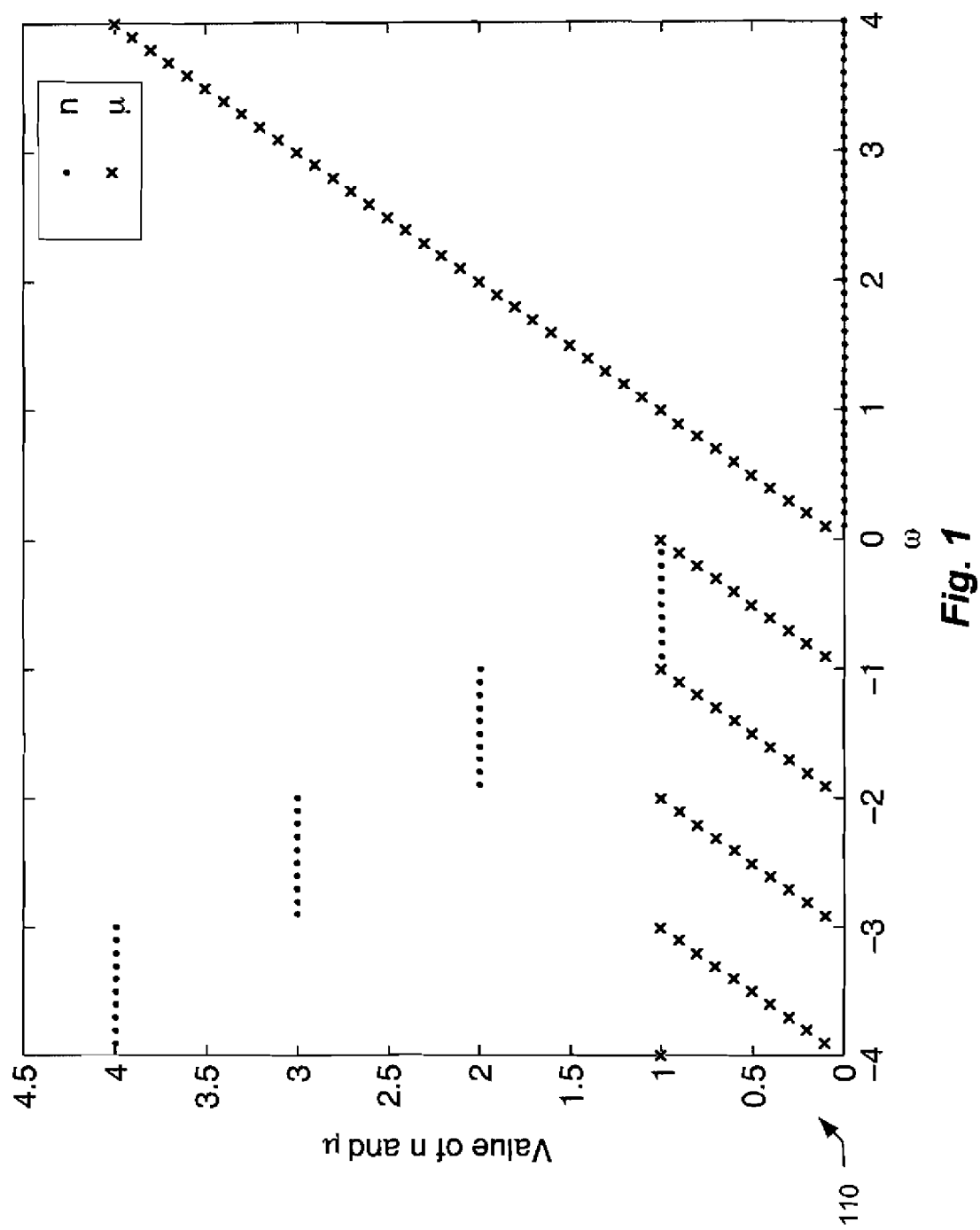
FIG. 1 is a plot showing the values of n and μ for different values of ω as determined by equation (8) herein.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, modified pulse sequences are provided that allow for the direct measurements of moments of relaxation-time or diffusion distributions. The data from these pulse sequences provides direct estimates of fluid properties such as average chain length and viscosity of a hydrocarbon. In comparison to the uniformly-spaced pulse sequence, these pulse sequences are faster and have a lower error bar in computing the fluid properties.

Co-pending U.S. Patent Application No. 61/242,218, filed Sep. 14, 2009 (incorporated herein by reference) describes a method to analyze NMR data that obviates the estimation of the $T_1$, $T_2$, or D distributions. A new mathematical formulation is described where the moments of a random variable can be directly computed from the measurement. The method has two distinct advantages: the computation of moments is linear and does not require prior knowledge or information of the expected distribution. A moment of a random variable x with density function $f_x(x)$ is defined as, $$\langle x^\omega \rangle \equiv \frac{\int_0^\infty x^\omega f_x(x) dx}{\int_0^\infty f_x(x) dx} \tag{6}$$

For NMR applications, the variable x corresponds to relaxation times $T_1$, $T_2$, or diffusion D. The moments of relaxation times or diffusion can be directly computed from the measured magnetization data, $$\langle x^\omega \rangle = \frac{(-1)^n}{\Gamma(\mu)\phi} \int_0^\infty t^{\mu-1} \left[ \frac{d^n M(t)}{dt^n} \right] dt, \omega = \mu - n \tag{7}$$

where $\Gamma(\ )$ represents the Gamma function and $$\phi = M(t=0) = \int_0^\infty f_x(x) dx.$$

The contribution of variable $\omega$ is in two parts: a real number $\mu$ and an integer n where the mathematical operator $t^{\mu-1}$ operates on the n-th derivative of the data. Given a value of $\omega$, the values of n and $\mu$ are unique and given as, $$\omega > 0: n=0, \mu=\omega$$

$$\omega \leq 0: \omega = \mu - n, 0 < \mu \leq 1, n = [-\omega] + 1 \tag{8}$$

where [$\omega$] refers to the integral part of real number $\omega$. FIG. 1 is a plot 110 showing the values of n and $\mu$ for different values of $\omega$ as determined by above these equations.

According to some embodiments, the computation of moments of relaxation times $T_1$, $T_2$, or diffusion D, in conjunction with the scaling laws, can lead to greatly improved alternative pulse sequences to specifically target or estimate only certain moments of relaxation time/diffusion. In co-pending U.S. Patent Application Publication No. 2008-0314582 (incorporated herein by reference), "targeted" measurements are described as measurements that target a certain specified parameter at a particular location in the reservoir space. These targeted measurements are achieved by both hardware and software modifications.

According to some embodiments, the concept of targeted measurements is applied to NMR data and alternate pulse sequences are described to directly estimate the moments of relaxation time or diffusion coefficients. According to some embodiments, alternate pulse sequences are designed by taking advantage of the specific exponential-kernel structure in eqn. (1) as well as the computation of moments using eqn. (7). The magnetization data from the new pulse sequences can be directly interpreted to obtain fluid properties.

According to some embodiments, further detail will now be provided for modified pulse sequences for measuring NMR data. The non-uniformly spaced pulse sequences are targeted to specifically measure one of the moments of the relaxation time $T_1$, $T_2$, or D distribution. For simplicity, consider that the random variable in eqn. (1) is $T_1$ and a specific $\omega$-th moment of $T_1$ is desired, where $\omega > 0$. This corresponds to the right-hand side of the $\omega$ axis in FIG. 1. In this case, from eqns. (7) and (8), $$\langle T_1^\omega \rangle = \frac{1}{\Gamma(\omega)\phi} \int_0^\infty t^{\mu-1} M(t) dt \tag{9}$$

We introduce a new variable where $$\tau = t^\omega \tag{10}$$

Therefore, eqn. (9) can be re-written as $$\langle T_1^\omega \rangle = \frac{1}{\Gamma(\omega+1)\phi} \int_0^\infty M_\tau(\tau) d\tau \tag{11}$$

where $M_\tau(\tau)$ is the magnetization data in the $\tau$ domain. Eqn. (11) indicates that if the data are acquired such that they are uniformly spaced in the $\tau$ domain, then the sum of the measured data directly provides the $\omega$-th moment. From eqn. (10), uniform spacing in the $\tau$ domain implies non-uniform spacing in the time (t) domain.

Figure 2:
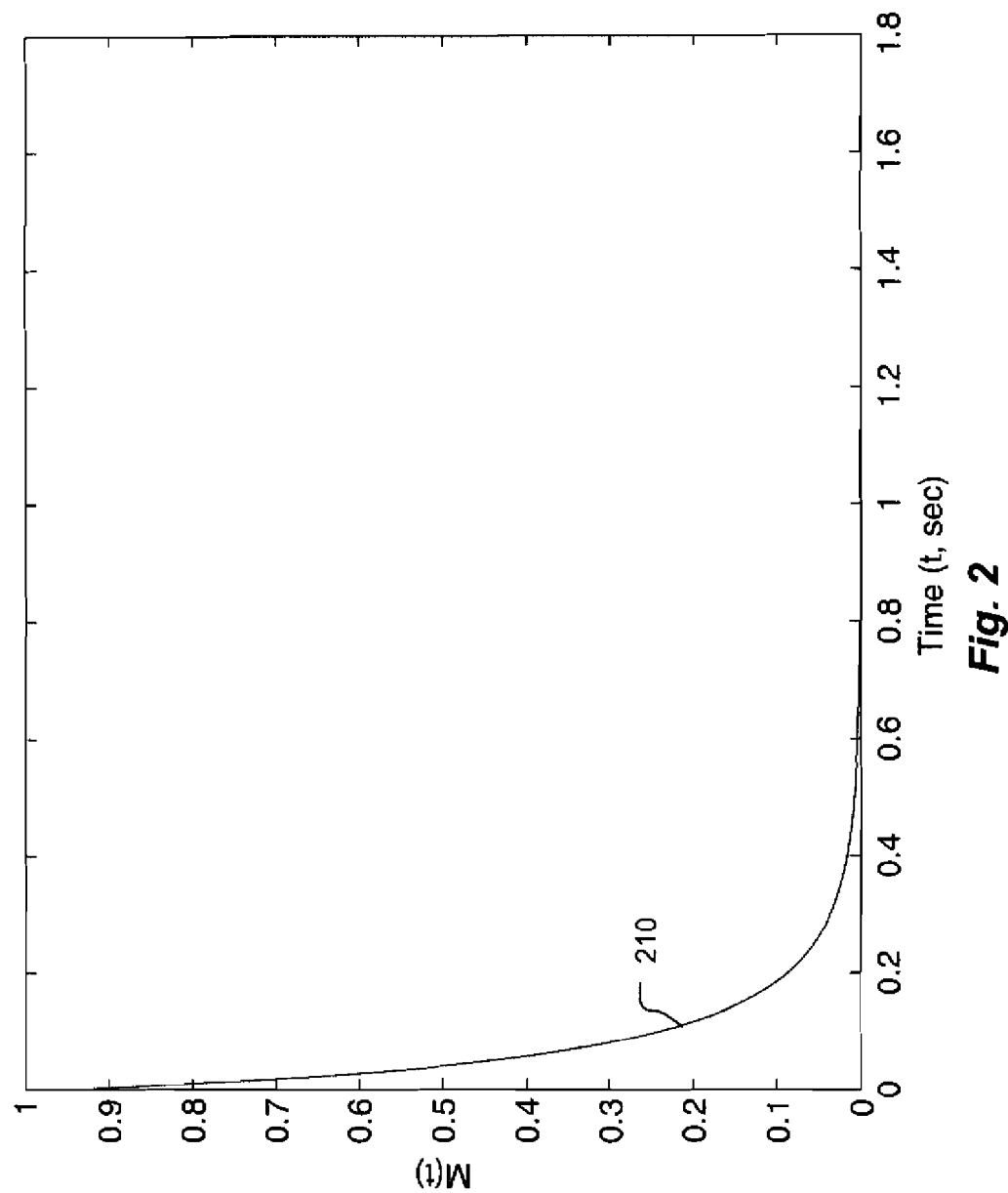
FIG. 2 is a plot showing an example of a single exponential acquired at uniform time intervals in the time-domain.
Figure 3:
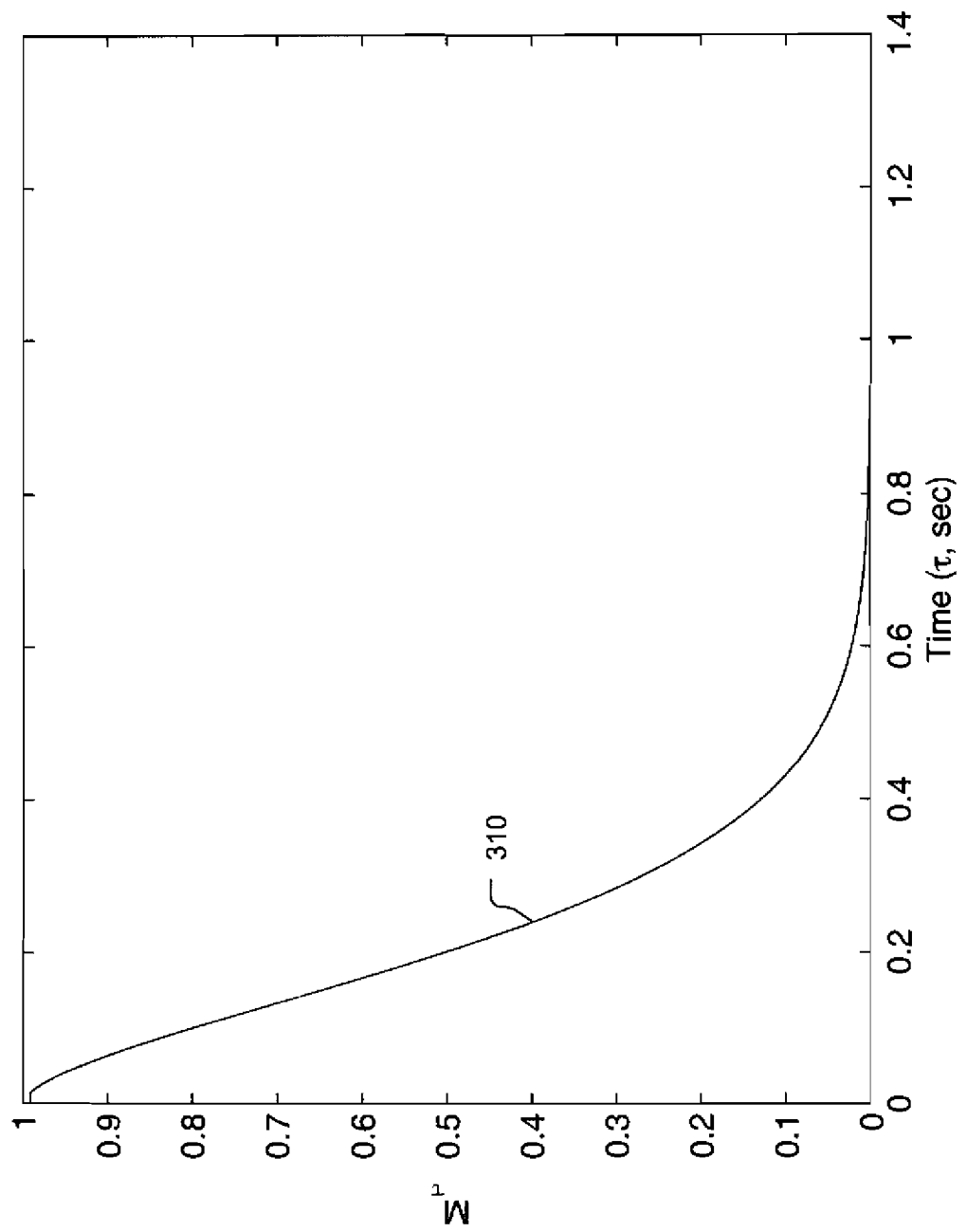
FIG. 3 is a plot showing a non-uniform sampling, according to some embodiments.
Figure 4:
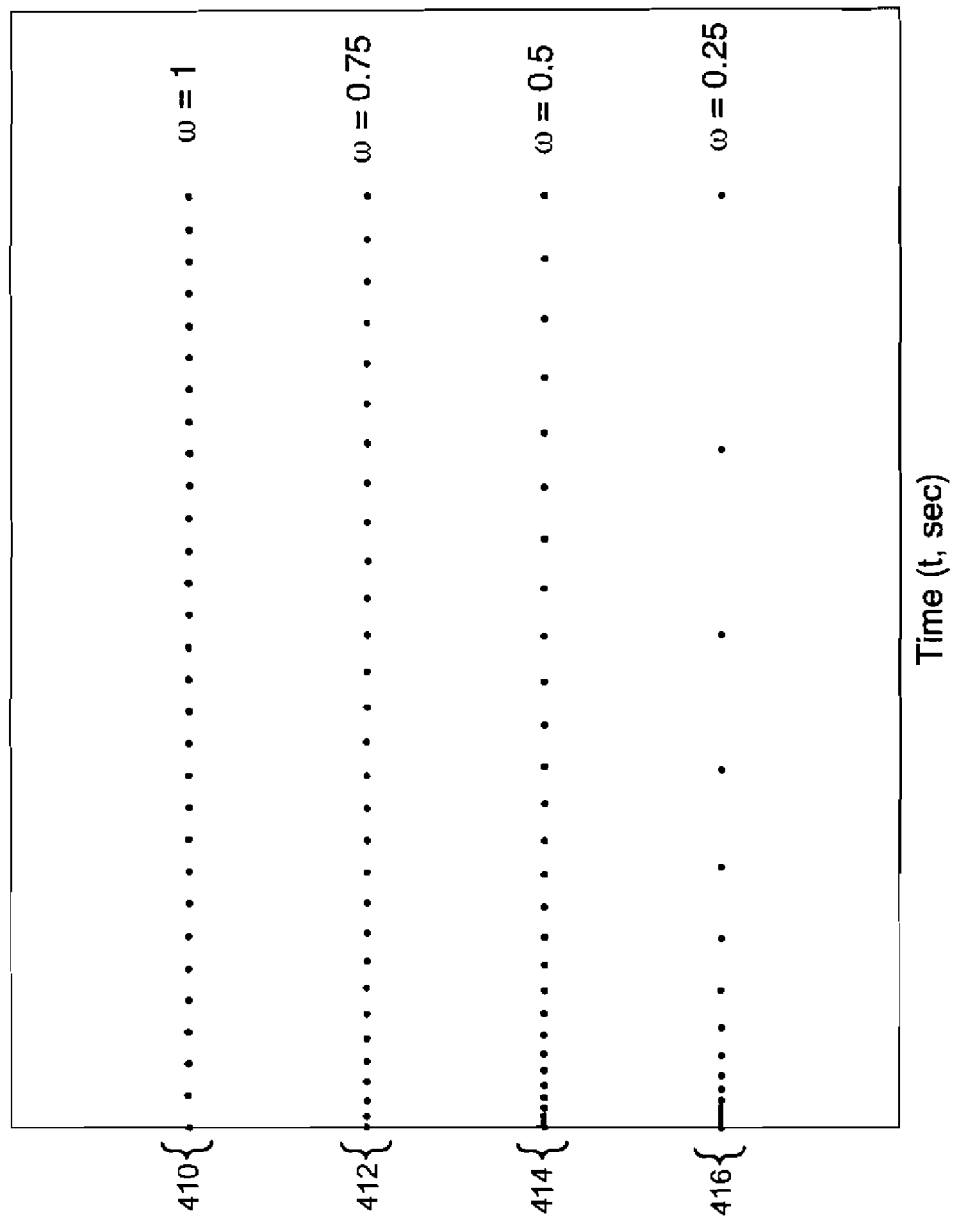
FIG. 4 plots examples of non-uniform sampling in time domain that can directly provide moments of relaxation or diffusion distribution, according to some embodiments.

We illustrate this with an example. FIG. 2 is a plot showing an example of a single exponential acquired at uniform time intervals in the time-domain. In particular, curve 210 plots a single exponential decay of the form $M(t)=e^{-t/T_1}$ in the time-domain as shown in where the data are uniformly sampled in time. In this example, suppose that the 0.5-th moment of $T_1$ is required. FIG. 3 is a plot showing a non-uniform sampling, according to some embodiments. In particular, using eqn. (10), the data shown by curve 310 are sampled uniformly in the $\sqrt{t}$ domain. Curve 310 is an example of a single exponential in the time-domain into a Guassian in the $\tau$ domain with $M(t)=e^{-\tau^2/T_1}$. Using eqn. (11), the sum of measured echoes of the Gaussian directly provides $\langle T_1^{0.5} \rangle$. Thus, if the $\omega$-th moment is desired, then the data need to be sampled non-uniformly in time according to eqn. (10). FIG. 4 plots examples of non-uniform sampling in time domain that can directly provide moments of relaxation or diffusion distribution, according to some embodiments. In particular, plots 410, 412, 414 and 416 represent sampling for $\omega$ values of 1, 0.75, 0.5, and 0.25 respectively. When $0<\Omega<1$, this leads to finer sampling at the initial part of the data and coarser sampling at the tail end of the data.

The concept of non-uniform sampling is also valid when $\omega<0$. Consider the case when $-1<\omega\leq 0$. In this case, eqn. (7) reduces to $$\langle T_1^\omega \rangle = \frac{-1}{\Gamma(\mu)\phi} \int_0^\infty t^{\mu-1} \left[ \frac{dM(t)}{dt} \right] dt \text{ where } \mu = 1+\omega > 0 \tag{12}$$

Eqn. (12) can be re-written as $$\langle T_1^\omega \rangle = \frac{-1}{\Gamma(\mu)\phi} \int_0^\infty t^{\mu-1} \left[ \frac{d[M(t)-M(0)]}{dt} \right] dt \tag{13}$$

Using integration by parts, $$\langle T_1^\omega \rangle = \frac{-1}{\Gamma(\mu)\phi}[t^{\mu-1}\{M(t) - M(0)\}]_{t=0}^{t=\infty} + \qquad (14)$$

$$\frac{(\mu-1)}{\Gamma(\mu)\phi}\int_0^\infty t^{\mu-2}[M(t) - M(0)]dt$$

$$= \frac{M(0)}{\phi}\delta_{\mu 1} + \frac{(\mu-1)}{\Gamma(\mu)\phi}\int_0^\infty t^{\mu-2}[M(t) - M(0)]dt \qquad (15)$$

where $\delta_{\mu 1}=1$ only if $\mu=1$ and is zero otherwise. When $\mu=1$ (corresponding to $\omega=0$), the first term in eqn. (15) is 1 (since $M(0)=\phi$) and the second term is zero. This is consistent with the definition of the zero-th moment in eqn. (6) with $\langle T_1^{\omega=0} \rangle =1$.

When $0<\mu<1$, the first term in eqn. (15) is zero. The second term is integrable at $t=0$ since $[M(t)-M(0)] \sim t$ as $t \to 0$. In this case, we introduce a new variable $\tau$ where $$\tau = t^{\mu-1} \qquad (16)$$

Here, $\tau \to \infty$ when $t \to 0$, and $\tau \to 0$ when $t \to \infty$. Therefore, eqn. (15) becomes $$\langle T_1^\omega \rangle = \frac{-1}{\Gamma(\mu)\phi}\int_0^\infty [M_T(\tau) - M(0)]d\tau \qquad (17)$$

Similar to eqn. (11), the area under the integrand $[M_T-M(0)]$ can be used to directly estimate the $\omega$-th moment. As shown herein below, the concept of the pulse sequence for $\omega>0$ and $-1<\omega\leq0$ is valid for other ranges of $\omega$ as well. For example, when $-2<\omega\leq-1$, pulse sequences that directly measure the $\omega$-th moment are obtained by Taylor series expansion of the data with second-order terms in eqn. (13). Higher-order terms in the Taylor series lead to further negative values of $\omega$. As shown herein below, when $\omega$ is not a negative integer, $\langle T_1^\omega \rangle$ can be obtained by sampling uniformly in the $\tau$ domain, where $$\tau = t^\omega \qquad (18)$$

When $\omega$ is a negative integer, from eqns. (7) and (8), the $\omega$-th moment is obtained by the $|\omega|$-th derivative of the data, $$\langle T_1^\omega \rangle = \frac{(-1)^{|\omega|}}{\phi}\frac{d^{|\omega|}M(t=0)}{dt^{|\omega|}} \qquad (19)$$

In addition to computing the moments directly, this modified pulse sequence also enables fluid properties such as the average chain length and viscosity to be directly estimated in a simple manner. Re-writing eqns. (3) and (4), the average chain length and viscosity can be computed from moments of $T_1$ or $T_2$ relaxation time or diffusion, as $$\overline{N} = [B^{-1/\kappa}\langle T_1^{1/\kappa}\rangle]^{-\frac{\kappa}{\gamma+\kappa}} \qquad (20)$$

$$\overline{N} = [A^{-1/\nu}\langle D^{1/\nu}\rangle]^{-\frac{\nu}{\nu+\beta}} \qquad (21)$$

$$\eta \propto \langle D^{-1}\rangle \Rightarrow \eta \propto [\langle T^{\frac{1}{k}}\rangle]^{\frac{\beta k-\gamma\nu}{\gamma+k}}\langle T_1^{-\frac{\nu}{k}}\rangle \qquad (22)$$

According to eqns. (20) and (21), the average chain length can be estimated from a modified pulse sequence to directly estimate the $(1/\kappa)$-th moment of relaxation time or $(1/\nu)$-th moment of diffusion. Similarly, viscosity can be estimated from two modified pulse sequences to directly estimate the $(1/\kappa)$-th and $(1/\nu)$-th moment of relaxation time. For diffusion data, the kernel in eqn. (1) is $e^{-Dt}$. Using eqn. (10) with $\omega=1$, the negative first moment of diffusion and viscosity are obtained.

In addition to directly providing the parameters of interest, these pulse sequences are optimized to estimate any desired moments of relaxation time and/or diffusion. In comparison to pulse sequences where the data is uniformly acquired in time, these pulse sequences can be used to acquire the data faster. For example, given $\omega>0$, the error-bar in the $\omega$-th moment of $T_1$ relaxation is, $$\sigma_{\langle T_1^\omega \rangle}\Big|_{\text{Uniform Sampling}} = \frac{\sigma_\epsilon}{\Gamma(\omega)\phi}t_E^\omega\sqrt{\sum_{n=1}^{N_e}n^{2\omega-2}} \qquad (23)$$

Here $N_e$ denotes the total number of echoes obtained from uniform sampling between a given lower and upper limit of relaxation time and $t_E$ corresponds to the spacing between the echoes. In the case of non-uniform sampling, the error-bar in the $\omega$-th moment is, $$\sigma_{\langle T_1^\omega \rangle}\Big|_{\text{Non-Uniform Sampling}} = \frac{\sigma_\epsilon}{\Gamma(\omega+1)\phi}\tau_E\sqrt{N_e} \qquad (24)$$

Figure 5:
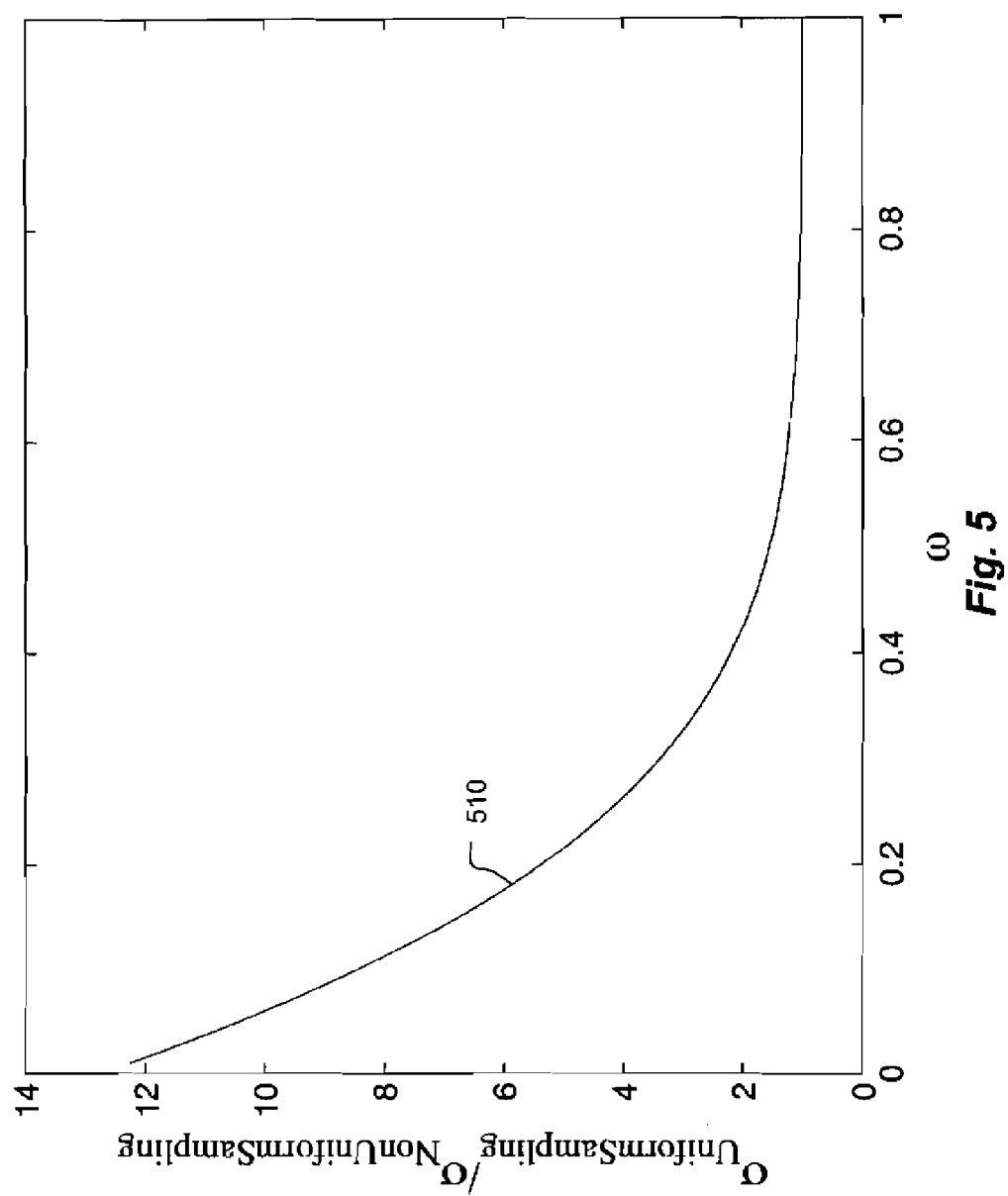
FIG. 5 is a plot showing the ratio of the error-bar in the moments obtained from uniform sampling to non-uniform sampling.

Here $\tau_E$ corresponds to the spacing between echoes in the $\tau$ domain. FIG. 5 is a plot showing the ratio of the error-bar in the moments obtained from uniform sampling to non-uniform sampling. There are two points to note from this curve 510. First, there is a significant advantage to non-uniform sampling as the error-bar in the computation of moments is lower (or at worst equal when $\omega=1$). Second, from eqns. (23) and (24), the standard deviation of noise for uniform sampling has to be smaller than that for non-uniform sampling to obtain a desired error-bar in the moments. Since the magnitude of the noise standard deviation in the data is inversely proportional to the square-root of the acquisition time, to achieve the same uncertainty in the parameter the data for non-uniform sampling can be acquired faster than that for uniform sampling.

Thus, according to some embodiments, a modified pulse sequence is provided that can directly provide moments of relaxation-time or diffusion distributions. This pulse sequence can be adapted to the desired moment of relaxation-time or diffusion coefficient. The data from this pulse sequence provides direct estimates of fluid properties such as average chain length and viscosity of a hydrocarbon. In general, in comparison with data acquired uniformly in time, this pulse sequence is faster and has a lower error bar in computing the fluid properties.

A general expression for the sampling rate of non-uniformly spaced pulse sequence will now be described in further detail, according to some embodiments. When $\omega$ is not a negative integer, $\langle T_1^\omega \rangle$ can be obtained by sampling uniformly in the $\tau$ domain, where $$\tau = t^\omega \qquad (25)$$

Proof: For $\omega>0$ and $1<\omega<0$, the proof has already been demonstrated in eqn. (11) and eqns. (12)-(17) respectively. When $-2<\omega\leq1$, from eqn. (8), n=2 and $\mu=\omega+2$. In this case, from eqn. (7), $$\langle T_1^\omega \rangle = \frac{1}{\phi\Gamma(\mu)} \int_0^\infty t^{\mu-1} \frac{d^2}{dt^2} M(t) dt \quad (26)$$

$$= \frac{1}{\phi\Gamma(\mu)} \int_0^\infty t^{\mu-1} \frac{d^2}{dt^2} [M(t) - M(0) - tM^{(1)}(0)] dt$$

$$= \frac{1}{\phi\Gamma(\mu)} \left[ t^{\mu-1} \frac{d}{dt} \{M(t) - M(0) - tM^{(1)}(0)\} \right]_{t=0}^{t=\infty} -$$

$$\frac{(\mu-1)}{\phi\Gamma(\mu)} \int_0^\infty t^{\mu-2} \frac{d}{dt} [M(t) - M(0) - tM^{(1)}(0)] dt$$

$$= -\frac{1}{\phi} M^{(1)}(0) \delta_{\mu 1} - \frac{1}{\phi\Gamma(\mu-1)}$$

$$[t^{\mu-2} \{M(t) - M(0) - tM^{(1)}(0)\}]_{t=0}^{t=\infty} +$$

$$\frac{(\mu-2)}{\phi\Gamma(\mu-1)} \int_0^\infty t^{\mu-3} [M(t) - M(0) - tM^{(1)}(0)] dt$$

$$= -\frac{1}{\phi} M^{(1)}(0) \delta_{\mu 1} + \frac{(\mu-2)}{\phi\Gamma(\mu-1)} \int_0^\infty t^{\mu-3}$$

$$[M(t) - M(0) - tM^{(1)}(0)] dt$$

$$= -\frac{1}{\phi} M^{(1)}(0) \delta_{\mu 1} + \frac{1}{\phi\Gamma(\omega)} \int_0^\infty t^{\omega-1}$$

$$[M(t) - M(0) - tM^{(1)}(0)] dt$$

where $\delta_{\mu 1}=1$ only when $\mu=1$ and is zero otherwise and $$M^1(t) = \frac{dM(t)}{dt}.$$

When $\mu=1$ (corresponding to $\omega=1$), the first term in eqn. (26) corresponds to the first derivative of the data at $t=0$ and is consistent with the definition of the negative first moment. In this case, the second term is zero. When $-2<\mu<1$, the first term in eqn. (26) is zero. The second term is integrable at $t=0$. Using eqn. (25), the area under the integrand $[M(t)-M(0)-tM^{(1)}(0)]$ can be used to directly estimate the $\omega$-th moment.

In general, when $n \geq 1$, eqn. (7) can be written as $$\langle T_1^\omega \rangle = \frac{(-1)^n}{\phi\Gamma(\mu)} \int_0^\infty t^{\mu-1} \frac{d^n}{dt^n} M(t) dt \quad (27)$$

$$= \frac{(-1)^n}{\phi\Gamma(\mu)} \int_0^\infty t^{\mu-1} M^{(n)}(t) dt$$

$$= \frac{(-1)^{n-1}}{\phi} M^{(n-1)}(0) \delta_{\mu 1} + \frac{1}{\phi\Gamma(\mu-n)} \int_0^\infty t^{\mu-n-1}$$

$$\left[ M(t) - \sum_{m=0}^{n-1} \frac{t^m}{m!} M^{(m)}(0) \right] dt$$

$$= \frac{(-1)^{n-1}}{\phi} M^{(n-1)}(0) \delta_{\mu 1} + \frac{1}{\phi\Gamma(\omega)} \int_0^\infty t^{\omega-1}$$

$$\left[ M(t) - \sum_{m=0}^{n-1} \frac{t^m}{m!} M^{(m)}(0) \right] dt$$

where $$M^{(m)}(t) = \frac{d^m}{dt^m} M(t) \quad (28)$$

and $$M^{(0)}(t) = M(t) \quad (29)$$

Note that:

$$M(t) - \sum_{m=0}^{n-1} \frac{t^m}{m!} M^{(m)}(0) \rightarrow t^n \text{ as } t \rightarrow 0 \quad (30)$$

As before, the first term in eqn. (27) is valid only for negative integer values of $\omega$ and corresponds to the $|\omega|$-th derivative of the data. For negative values of $\omega$ where $n<\omega<(n-1)$, the first term in eqn. (27) is zero. Using eqn. (25), the area under the integrand $$\left[ M(t) - \sum_{m=0}^{n-1} \frac{t^m}{m!} M^{(m)}(0) \right]$$

in the $\tau$ domain directly provides the $\omega$-th moment of relaxation time.

Figure 6A:
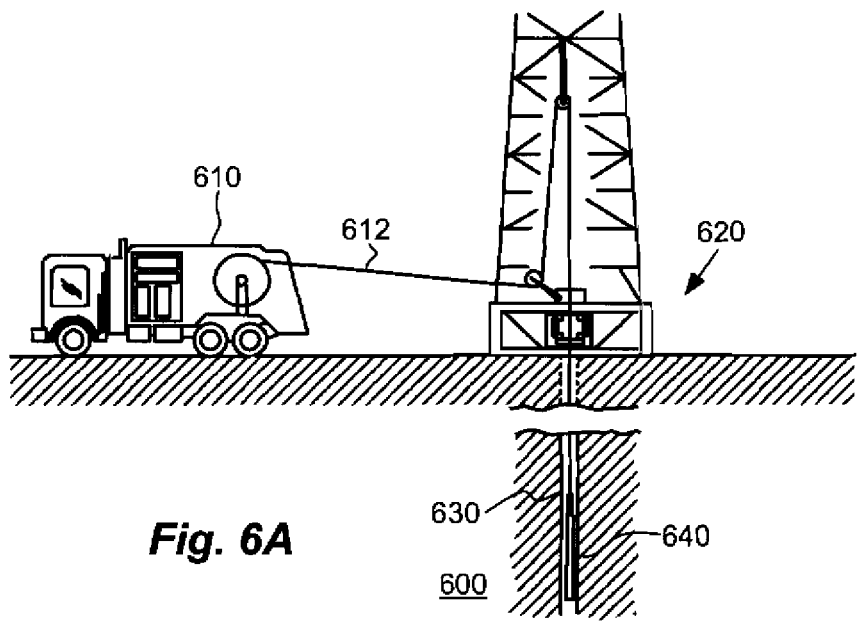
FIG. 6A shows an NMR tool being deployed in a wellbore, according to embodiments.

FIG. 6A shows an NMR tool being deployed in a wellbore, according to embodiments. Wireline truck 610 is deploying wireline cable 612 into well 630 via well head 620. Wireline tool 640 is disposed on the end of the cable 612 in a subterranean formation 600. Tool 640 includes an NMR tool, such as Schlumberger's Combinable Magnetic Resonance (CMR) Tool, or Schlumberger's MR Scanner Tool. According to some embodiments the NMR tool is combined with other downhole tools such as Schlumberger's Modular Formation Dynamics Tester downhole sampling tool. According to some embodiments, the NMR tool uses a pulse sequence as described herein. Data from the NMR tool can be recorded and/or processed downhole within tool 640, and/or can be transmitted to wireline truck 610 for recording and/or processing. According to embodiments, the NMR tool can be controlled, including the selection of pulse sequences, locally with processing systems within tool 640 and/or from the surface using processing systems for example in wireline truck 610.

Figure 6B:
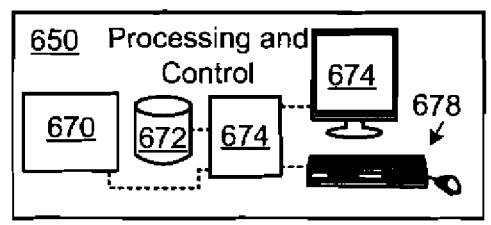
FIG. 6B is a schematic of a processing system used to control, record and process data from an NMR tool.

FIG. 6B is a schematic of a processing system used to control, record and process data from an NMR tool. Processing system 650 includes one or more central processing units 674, storage system 672, communications and input/output modules 670, a user display 676 and a user input system 678. Input/output modules 670 include modules to communicate with and control the NMR tool such that modified pulse sequences can be used as described herein.

Figure 7:
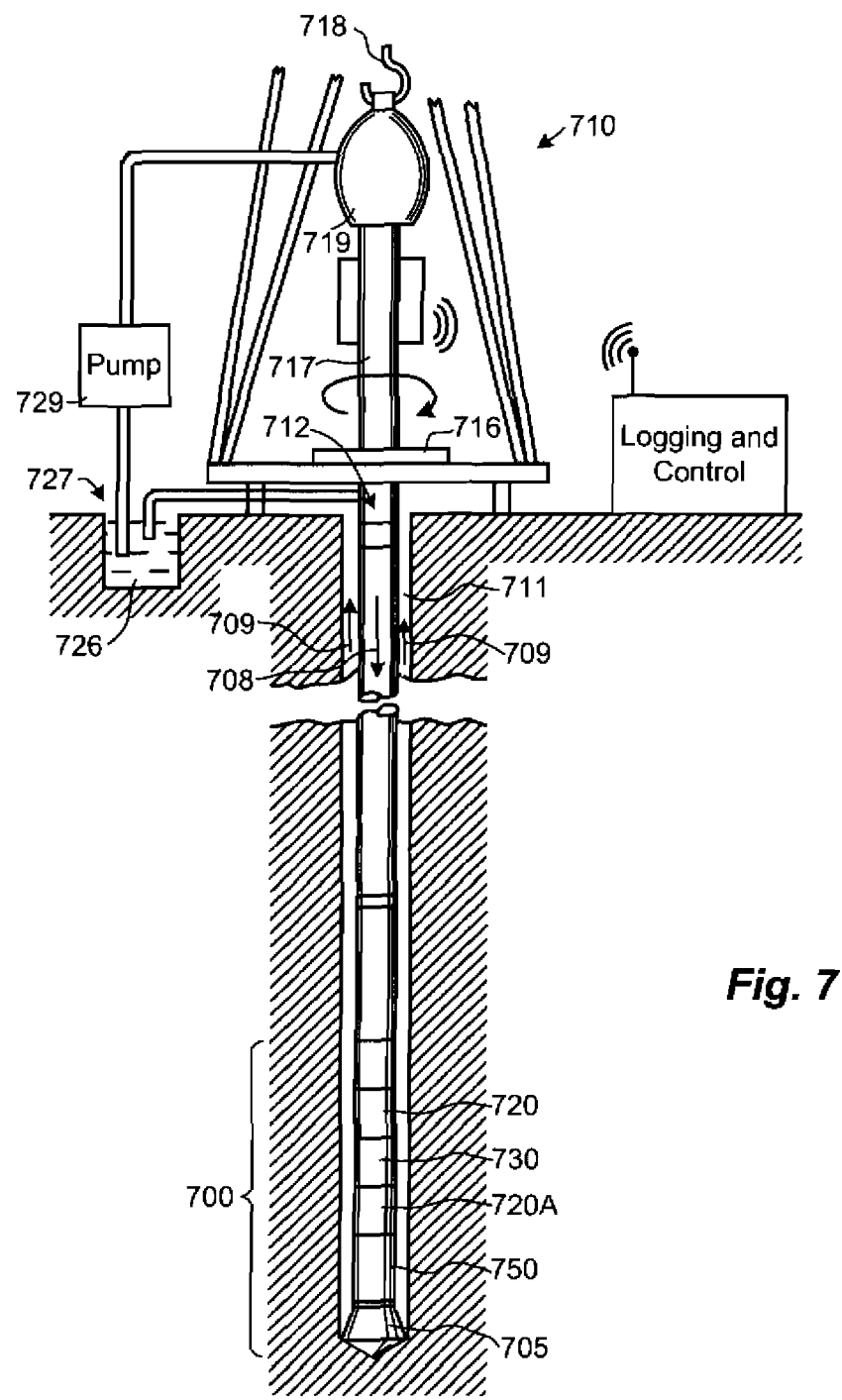
FIG. 7 illustrates another example of a wellsite system in which an NMR tool can be employed, according to some embodiments.

FIG. 7 illustrates another example of a wellsite system in which an NMR tool can be employed, according to some embodiments. The wellsite can be onshore or offshore. In this exemplary system, a borehole 711 is formed in subsurface formations by rotary drilling in a manner that is well known. Embodiments of the invention can also use directional drilling, as will be described hereinafter.

A drill string 712 is suspended within the borehole 711 and has a bottom hole assembly 700 which includes a drill bit 705 at its lower end. The surface system includes platform and derrick assembly 710 positioned over the borehole 711, the assembly 710 including a rotary table 716, kelly 717, hook 718 and rotary swivel 719. The drill string 712 is rotated by the rotary table 716, energized by means not shown, which engages the kelly 717 at the upper end of the drill string. The drill string 712 is suspended from a hook 718, attached to a traveling block (also not shown), through the kelly 717 and a rotary swivel 719 which permits rotation of the drill string relative to the hook. As is well known, a top drive system could alternatively be used.

In the example of this embodiment, the surface system further includes drilling fluid or mud 726 stored in a pit 727 formed at the well site. A pump 729 delivers the drilling fluid 726 to the interior of the drill string 712 via a port in the swivel 719, causing the drilling fluid to flow downwardly through the drill string 712 as indicated by the directional arrow 708. The drilling fluid exits the drill string 712 via ports in the drill bit 705, and then circulates upwardly through the annulus region between the outside of the drill string and the wall of the borehole, as indicated by the directional arrows 709. In this well known manner, the drilling fluid lubricates the drill bit 705 and carries formation cuttings up to the surface as it is returned to the pit 727 for recirculation.

The bottom hole assembly 700 of the illustrated embodiment a logging-while-drilling (LWD) module 720, a measuring-while-drilling (MWD) module 730, a roto-steerable system and motor, and drill bit 705.

The LWD module 720 is housed in a special type of drill collar, as is known in the art, and can contain one or a plurality of known types of logging tools. It will also be understood that more than one LWD and/or MWD module can be employed, e.g. as represented at 720A. (References, throughout, to a module at the position of 720 can alternatively mean a module at the position of 720A as well.) The LWD module includes capabilities for measuring, processing, and storing information, as well as for communicating with the surface equipment. In the present embodiment, the LWD module includes an NMR tool such as Schlumberger's ProVISION NMR tool.

The MWD module 730 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, and an inclination measuring device.

According to some embodiments, the techniques described herein are applied to estimate properties from other types of excitations than NMR. For example the techniques can be applied to other types of data where excitations induce an exponential decay. According to some embodiments, the techniques are applied to inducing a non-uniform sequence of pressure changes in a material. According to some other embodiments, the techniques are applied to induce a non-uniform sequence of temperature changes in a material.

While many examples have been described herein with respect to designing interval spacings in the time domain, according to some embodiments, the techniques described herein are applied to interval spacings in other domains, such as designing interval spacings in the frequency domain.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A method of estimating a property of a material comprising:
    inducing a measurable change in the material;
    making measurements of a material response to the induction, the material response exponentially decaying following the induction;
    repeating the induction at predetermined intervals;
    estimating the property of the material at least in part on the measurements of the exponentially decaying material response, the predetermined intervals being designed and modified based on the measurement of the exponentially decaying material response so as to improve the estimation of the property.

2. A method according to claim 1 wherein the induction is an excitation of the material.

3. A method according to claim 2 wherein the induction is a transmitted transverse magnetic pulse.

4. A method according to claim 2 wherein the induction is an applied pressure pulse.

5. A method according to claim 2 wherein the induction is the induction of a temperature change in the material.

6. A method according to claim 1 wherein an interval spacing in time is designed according to a formula determined by the property being estimated.

7. A method according to claim 1 wherein an interval spacing in a frequency domain is designed according to a formula determined by the property being estimated.

8. A method according to claim 1 wherein an interval spacing of the induction is non-uniform in both linear and logarithmic scales.

9. A method according to claim 1 wherein an interval spacing of the induction in time is predetermined using a power law.

10. A method according to claim 1 wherein an interval spacing of the induction in a frequency domain is predetermined using a power law.

11. A method according to claim 1 wherein an interval spacing in time is selected for the property to be directly computed from the measurements.

12. A method according to claim 1 wherein an interval spacing in a frequency domain is selected for the property to be directly computed from the measurements.

13. A method according to claim 1 wherein the method is carried out as part of one or more oilfield services.

14. A method according to claim 13 wherein the measurements are made downhole.

15. A method according to claim 13 wherein the measurements are made on the surface.

16. A method according to claim 1 wherein the material is a fluid.

17. A method according to claim 16 wherein the properties are fluid properties.

18. A method according to claim 1 wherein the material is one or more rock solids and the properties are petrophysical properties of the one or more rock solids.

19. A method according to claim 18 wherein the induction is nuclear magnetic resonance and the property is a moment of relaxation-time or diffusion distribution.

20. A method according to claim 1 wherein the material is a mixture of solid and liquid.

21. A method according to claim 20 wherein the properties are fluid and petrophysical properties in porous solids.

22. A system for estimating a property of a material comprising:
- an inducer that is adapted to induce a measurable change in the material;
- one or more sensors adapted to measure a material response that tends to exponentially decay following the induction;
- a controller coupled to the inducer, adapted and programmed to repeat the induction at predetermined intervals; and
- a processing system adapted to estimate the property of the material at least in part on the one or more sensor measurements, wherein the predetermined intervals are designed and modified based on the measurement of the exponentially decaying material response so as to improve the estimation of the property.

23. A system according to claim 22 wherein the inducer induces an excitation of the material.

24. A system according to claim 23 wherein the inducer transmits a transverse magnetic pulse using an antenna.

25. A system according to claim 23 wherein the inducer applies a pressure pulse.

26. A system according to claim 23 wherein the inducer induces a temperature change in the material.

27. A system according to claim 22 wherein an interval spacing in time is designed according to a formula determined by the property to be estimated.

28. A system according to claim 22 wherein an interval spacing in a frequency domain is designed according to a formula determined by the property to be estimated.

29. A system according to claim 22 wherein the intervals are non-uniform in both linear and logarithmic scales.

30. A system according to claim 22 wherein the intervals is predetermined using a power law.

31. A system according to claim 22 wherein the intervals are selected for the property to be directly computed from the measurements.

32. A system according to claim 22 wherein the system is carried out as part of one or more oilfield services.

33. A system according to claim 32 further comprising a downhole deployable tool body that houses the inducer and the sensors.

34. A system according to claim 32 further comprising a surface instrument that houses the inducer and the sensors.

35. A system according to claim 22 wherein the material is a fluid.

36. A system according to claim 35 wherein the properties are fluid properties.

37. A system according to claim 22 wherein the material is one or more rock solids and the properties are petrophysical properties of the one or more rock solids.

38. A system according to claim 37 wherein the induction is nuclear magnetic resonance and the property is a moment of relaxation-time or diffusion distribution.

39. A system according to claim 22 wherein the material is a mixture of solid and liquid.

40. A method according to claim 39 wherein the properties are fluid properties in porous solids.

* * * * *